United States Patent
Canales Espinosa De Los Monteros et al.

(10) Patent No.: US 8,124,546 B2
(45) Date of Patent: Feb. 28, 2012

(54) NON-WOVEN FABRIC THAT ACTS AS AN INDICATOR

(76) Inventors: Carlos Canales Espinosa De Los Monteros, Puebla (MX); Bernardo Fajardo Eslaba, Puebla (MX)

( * ) Notice: Subject to any disclaimer, the term of this patent is extended or adjusted under 35 U.S.C. 154(b) by 0 days.

(21) Appl. No.: 12/092,541

(22) PCT Filed: Nov. 3, 2006

(86) PCT No.: PCT/MX2006/000120
§ 371 (c)(1),
(2), (4) Date: Jul. 11, 2008

(87) PCT Pub. No.: WO2007/053001
PCT Pub. Date: May 10, 2007

(65) Prior Publication Data
US 2008/0305700 A1   Dec. 11, 2008

(30) Foreign Application Priority Data
Nov. 4, 2005   (MX) ................. PA/a/2005/011978

(51) Int. Cl.
*B32B 3/00* (2006.01)
(52) U.S. Cl. .......................................... 442/59; 428/690
(58) Field of Classification Search ........... 442/59
See application file for complete search history.

(56) References Cited

U.S. PATENT DOCUMENTS

| | | | |
|---|---|---|---|
| 5,182,316 A * | 1/1993 | DeVoe et al. | 522/99 |
| 5,246,862 A * | 9/1993 | Grey et al. | 436/28 |
| 5,294,375 A * | 3/1994 | Kampe et al. | 252/583 |
| 5,643,588 A | 7/1997 | Roe et al. | |
| 5,693,037 A | 12/1997 | Lee et al. | |
| 5,709,747 A | 1/1998 | Goldwasser | |
| 5,830,487 A | 11/1998 | Klofta et al. | |
| 5,856,245 A | 1/1999 | Caldwell et al. | |
| 5,863,887 A | 1/1999 | Gillette | |
| 5,885,656 A | 3/1999 | Goldwasser | |
| 5,938,649 A | 8/1999 | Ducker et al. | |
| 6,049,024 A | 4/2000 | Thomas et al. | |
| 6,183,847 B1 | 2/2001 | Goldwasser | |
| 6,287,581 B1 | 9/2001 | Krzysik et al. | |
| 2003/0087566 A1 * | 5/2003 | Carlyle et al. | 442/59 |
| 2004/0117916 A1 * | 6/2004 | Polanco et al. | 8/115.51 |
| 2006/0293205 A1 * | 12/2006 | Chung | 510/383 |

FOREIGN PATENT DOCUMENTS

| | | |
|---|---|---|
| MX | 191385 | 3/1999 |
| MX | PA/A/2003/00100 | 12/2002 |
| MX | PA/A/2004/000086 | 12/2003 |
| MX | PA/A/2004/000087 | 12/2003 |
| MX | 249176 | 9/2007 |
| MX | PA/A/2004/006371 | 8/2008 |
| WO | 03/041626 A1 | 5/2003 |

* cited by examiner

*Primary Examiner* — Lynda Salvatore
(74) *Attorney, Agent, or Firm* — Fitch, Even, Tabin & Flannery, LLP

(57) ABSTRACT

A non-woven fabric to be used in a disposable absorbent article is disclosed, to which a formula is added during its manufacturing process, either to change its affinity to water and/or to provide same with any desired characteristic, said formula containing an indicator means such that the formula can be detected along the entire length and width of the fabric during the manufacturing process thereof, without the need of carrying out laboratory tests. The indicator means can be an optical indicator, a thermal indicator or a coloring agent.

14 Claims, 1 Drawing Sheet

NON-WOVEN FABRIC THAT ACTS AS AN INDICATOR

TECHNICAL FIELD

A non-woven material is a fabric consisting of an assembly of textile fibers which are attached to each other by means of a mechanical attachment, by means of melting or by external means such as an adhesive, a latex, synthetic resins, and the like. The fibers may be oriented in the same direction, randomly oriented or selectively oriented.

The processes for the manufacture of a non-woven fabric can be grouped in textile processes, processes alike to the manufacture of paper, extrusion, or a combination of the latter. Textile processes are basically aerodynamic carding and forming of fabrics with the fibers selectively oriented. Fabrics made by this system are known as "drylaid" or "airlaid" non-woven fabrics. Fabrics made by means of a process similar to the manufacture of paper are known as "wetlaid" fabrics. Processes by means of extrusion include "spunbond" and "meltblown"; non-woven fabrics of this type are manufactured with machinery associated to polymer extrusion.

Among many other uses, non-woven fabrics are used in the manufacture of disposable absorbent articles as their topsheet, backsheet, transfer layer and/or anti-leakage lateral cuffs or barriers, among other components.

When used as the topsheet of a disposable absorbent article, such as a disposable diaper, a sanitary napkin, training pants or a panty-liner, a non-woven fabric may be formed by natural or synthetic fibers and may be made by any known method. In this case, it is convenient that the fabric permits liquids to pass through and prevent or avoid their return, for which it is necessary to use fibers made of a hydrophobic material in its manufacture; once the fabric is made, it can be treated so to provide same with a desired level of hydrophilic or hydrophobic character in the entire fabric or in certain zones thereof. As an example, it is desired that the fabric be hydrophilic in the central portion of the article and hydrophobic in the lateral portions thereof. On the other hand, the application to the top of the non-woven fabric that forms the topsheet of this kind of articles of some type of treatment to protect the skin of the user has become common. For this purpose, a formula is applied to the non-woven fabric, such that during use same is in contact with the skin and may transfer thereto.

There are several patents relating to the application of some type of formula containing a surfactant to treat a non-woven fabric and change its affinity to water; the surfactant may be applied by any conventional method, such as immersed spraying, printing, brushing or similar techniques. Some patents related to this topic are: U.S. Pat. Nos. 6,183,847; 5,709,747 and 5,885,656, all of them assigned to Avgol Non Woven Industries, which disclose different methods of changing affinity to water in a non-woven fabric in certain zones thereof; U.S. Pat. No. 6,049,024, assigned to BBA Non Wovens, discloses a non-woven fabric with the central zone thereof treated with a surfactant to render same hydrophilic; international publication WO 03/041626, pertaining to Paragon Trade Brands, describes a disposable absorbent article having a topsheet which is selectively pervious with a treated, hydrophilic central zone, and hydrophobic lateral zones; Mexican Patent No. 191,385 describes a disposable absorbent article, such as a disposable diaper, comprising a topsheet comprised of three zones, a pervious central zone and impervious lateral zones; Mexican Patent Application No. PA/a/2003/000100, assigned to Grupo P. I. Mabe, describes a process to obtain a non-woven fabric with permeability zones.

On the other hand, there are also many patents related to the application of some type of formula to a non-woven fabric in order to protect the skin of the user during use of an absorbent disposable article. Some examples of the most relevant ones are: U.S. Pat. No. 5,643,588, assigned to Procter & Gamble, which discloses a disposable diaper with a topsheet impregnated with a lotion containing an emollient and also a surfactant; U.S. Pat. No. 5,693,037, also assigned to Procter & Gamble, disclosing the use of a silicon-based surfactant; U.S. Pat. No. 5,830,487, assigned to Procter & Gamble, which discloses a lotion which is applied to the topsheet, said lotion containing an organic acid, such a citric acid, and hydrophilic solvents, such as propylene glycol, so to kill virus and provide softness; U.S. Pat. No. 5,938,649, assigned to Drypers Corporation, discloses the use of aloe vera on the topsheet of a disposable absorbent article; U.S. Pat. No. 6,287,581, assigned to Kimberly-Clark, which describes the use, on the surface of an article of this kind, of a lipid-enriched hydrophobic composition, comprising a natural oil, an sterol, a surfactant, a moisturizing agent, and an emollient; Mexican Patent Applications 9810294, PA/a/2004/000087, PA/a/2004/000086, and PA/a/2004/006371, all of them assigned to Grupo P. I. Mabe, describing different formulations to be applied to the topsheet, each of them for specific purposes.

During the process of manufacture of a non-woven fabric, the formula is applied thereto by means of different methods: soaking, spraying, plastering, and the like. This application may fail due to several reasons, resulting in a non-homogeneous application or leaving zones of the fabric without same. Presently there is no easy, quick and inexpensive manner of assuring that the application of a formula whatsoever to a non-woven fabric is homogeneous and covers the zone or zones of the fabric where it is required. As a result, the present invention resolves the mentioned problem and embodies the addition of indicator means to any type of formula to be applied to a non-woven fabric, either to change its affinity to water, to soften same, to help protect the skin of the user, to control bad odor, and the like, so that this application can be detected, either at plain sight or by external means. The indicator means must be soluble in the formula and should not affect its function, as well as not causing soreness in the skin of the user. Preferably, optical indicators which become visible with certain types of light are used; indicator means which become visible upon a change in pH can also be used, indicator means visible at a certain temperature or any other type of indicator means.

OBJECTS OF THE INVENTION

An object of the present invention is to detect in a quick and safe manner the application of any kind of formula to a non-woven fabric.

Another object of the present invention is that said application of a formula be detected by indicator means which is added to said formula.

A further object of the present invention is that said indicator means does not alter the chemical characteristics of the formula in question.

Another object of the present invention is that the application of any formula to a non-woven fabric can be detected during the process of manufacture of the fabric itself.

DETAILED DESCRIPTION OF THE INVENTION

Figure 1:
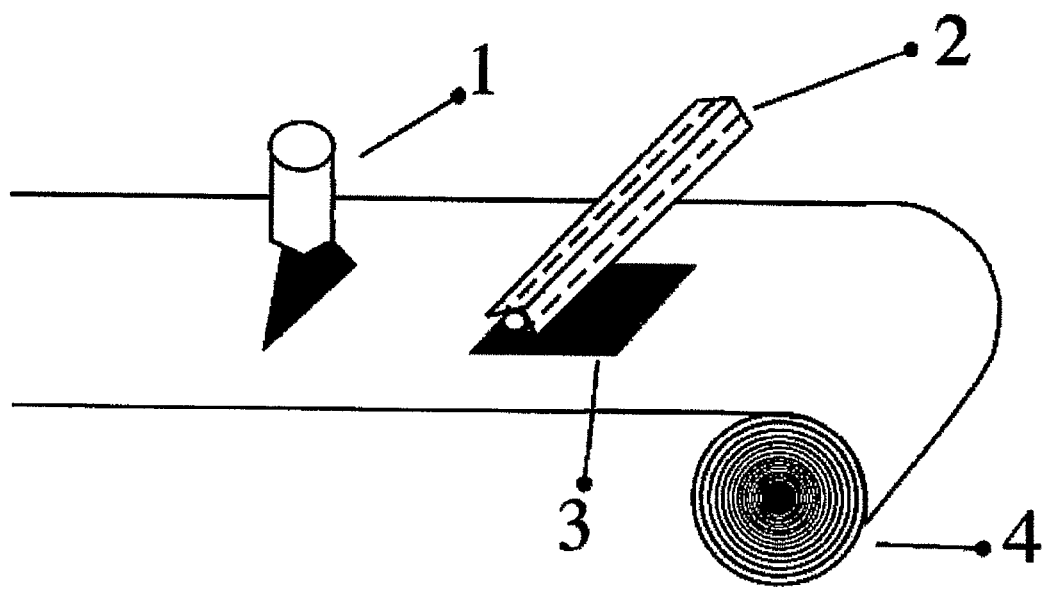
FIG. 1 illustrates the manner in which the indicator function operates in non-woven fabrics in a manufacturing line therefor.

Non-woven fabrics are a raw material commonly used in the manufacture of disposable absorbent articles and, as such, can be used as a topsheet, backsheet, transfer layer, to form anti-leakage lateral cuffs or barriers, in fastening tapes, and the like.

When a non-woven fabric is used as a topsheet in these articles, it is common to apply over same some type of formula, either to change its affinity to water, to provide same with more softness, to apply any treatment that may be transferred to the skin of the user during the use of the article, or for any other purpose. Generally, the formula is applied to the non-woven fabric once same has been formed by any method and before it is wound in reels.

The formula that is applied to the non-woven fabric generally has no color and, once it has been applied, it cannot be detected at plain sight, but rather it is necessary to carry out laboratory tests to verify its presence. In order to carry out the tests, parts of the fabric are selected and analyzed; however, it is not possible to assure a continuous and constant application to the entire fabric, since it is only detected in regard to the part of the fabric tested in the laboratory.

In order to overcome this problem, the present invention relates to the addition of indicator means to a formula to be applied to a non-woven fabric, such that the application can be detected during the manufacture process of the fabric, immediately after the application thereof and in the entire area of application, in order to be able to make corrections or adjustments, in which they are required, thus assuring a constant quality. The indicator means, preferably, is an optical indicator means which can be detected by means of ultraviolet or infrared light, such as an indicator means based on fluorophore compounds. Compounds of this type, while colorless, strongly absorb light having a lower wavelength in the ultraviolet and fluorescent region, that is, they emit light having a higher wavelength in the visible region of the light spectra. In this manner, by simply installing an ultraviolet or infrared lamp after the application of the formula to the non-woven fabric, such that the fabric passes, during the manufacturing process, and prior to be wound, under the lamp, it can be detected at plain sight if the application was homogeneous and if it was carried out in the zone or zones of the fabric where it is required, such as shown in FIG. 1, which schematically shows a part of the manufacturing process of a non-woven fabric, to which a formula containing an indicator means in accordance with the present invention is added by means of spraying (1); after the application of said indicator means, an ultraviolet or infrared lamp (2) is placed, depending on the type of indicator means added, along the entire width of the application area or zone, such that it can be detected, at plain sight, while the fabric passes under the lamp (2), if the application was homogeneous and it was carried out correctly in the zone or zones of the fabric where it is required. As an example, in FIG. 1 the application becomes apparent upon passing the fabric under the lamp (2) in the central zone (3) of the fabric. The lamp (2) is disposed prior to the fabric being wound (4). In this manner, corrections to the application of the formula can be made immediately, preventing the production of the fabric without the desired specifications, which involves high waste costs. On the other hand, the proposed process is simple, economical and easy to implement.

The coloring agents of this kind (fluorophore compounds) are not irritants when they are used in connection with fabrics that will be in contact with the skin; they are generally fluorophore compounds with a diaminoethylbenzene nucleus to which stabilizing groups are added, condensates with diaminoethyl-benzenesulphonic acid and derivatives thereof, from the ethyl benzene distyrodiphenyl families and their anionic derivatives.

Indicator means in accordance with the present invention that can be used herein include thermal indicator means, which become visible at certain temperatures, generally from about 25° C. to about 80° C., such as those belonging to the families of indigoiles and tioindigoiles as well as cupric phtalocyanines, tiazoles, toluenediamines, quinaphtalones, alizarines, naphtoles, diazonaphtoles and derivatives thereof; such that, once the formula with the indicator means is applied to the non-woven fabric, the latter is passed through a zone at a temperature at which the indicator means becomes visible and the application may thus be detected.

Finally, in another embodiment of the present invention, any kind of coloring agent visible at plain sight may be used as indicator means, particularly a coloring agent suitable to be used in contact with the skin and which is soluble in the formula to be added to the non-woven fabric, such as azo compounds, anilines, acroleines, quinoleines, acetanilines, dimethylanilines, dihydroxianthraquinones, nitrobenzene, dinitro-ethyidibenzyldisulphonic compounds, alpha and beta pirasolones, naphtoles, beta hydroxiethylanilines, and derivatives thereof; such that the zone or zones of the fabric where the formula is applied remain painted of the color of the coloring agent added. Thus, it can be detected at plain sight whether the application was suitable or not, if the color of the fabric is homogeneous and there are no colorless zones, if the formula is being applied properly. This alternative is useful when a colored non-woven fabric is desired.

The minimum concentration of the indicator means in the formula es of about 0.001% for any of the alternatives described herein, by way of example.

While the invention has been described as a function of its currently preferred embodiments, the scope thereof comprises any change or modification thereto that is apparent to a person skilled in the art.

The invention claimed is:

1. A non-woven fabric product configured for use in a disposable absorbent article, the non-woven fabric product comprising:
   a non-woven fabric; and
   a blend of treatment formula and optical indicator composition which is soluble in the treatment formula, visible under ultraviolet or infrared light and not reactive with the treatment formula, the blend applied to the non-woven fabric in amounts which are effective to make the optical indicator composition visible under ultraviolet or infrared light and to allow the determination of the uniformity of the application of the blend and treatment formula to the non-woven fabric, wherein the indicator composition is a fluorophore based indicator with a diaminoethylbenzene nucleus containing a stabilizing agent.

2. The non-woven fabric product according to claim 1, wherein the stabilizing agent is a diaminoethylbenzene-disulphonic acid or derivative thereof.

3. A non-woven fabric product configured for use in a disposable absorbent article, the non-woven fabric product comprising:
- a non-woven fabric; and
- a blend of a treatment formula and thermal indicator composition which is soluble in the treatment formula, visible at a temperature between 25° C. and 80° C., and not reactive with the treatment formula, the blend applied to the non-woven fabric in amounts which are effective to make the thermal indicator composition visible between 25° C. and 80° C. and to allow the determination of the uniformity of the application of the blend and treatment formula to the non-woven fabric.

4. The non-woven fabric product according to claim 3, wherein the thermal indicator composition is selected from the group consisting of indigoiles, tioindigoiles, cupric phtalocyanines, tiazoles, toluenediamines, quinaphtalones, alizarines, naphtoles, diazonaphtoles and derivatives thereof.

5. The non-woven fabric product according to claim 1, wherein the indicator composition is present in the treatment formula in a minimum amount of about 0.001%.

6. The non-woven fabric product according to claim 1, wherein the treatment formula applied to the non-woven fabric is effective to change the non-woven fabric's affinity to water.

7. The non-woven fabric product according to claim 2, wherein the indicator composition is present in the treatment formula in a minimum amount of about 0.001%, and the treatment formula is effective to change the affinity of the non-woven fabric to water.

8. The non-woven fabric product according to claim 3, wherein the indicator composition is present in the treatment formula in a minimum amount of about 0.001%.

9. The non-woven fabric product according to claim 3, wherein the treatment formula is effective to change the non-woven fabric's affinity to water.

10. The non-woven fabric product according to claim 4, wherein the indicator composition is present in the treatment formula in a minimum amount of about 0.001%.

11. The non-woven fabric product according to claim 4, wherein the treatment formula is effective to change the non-woven fabric's affinity to water.

12. A non-woven fabric product configured for use in a disposable absorbent article, the non-woven fabric product comprising:
- a non-woven fabric; and
- a blend of treatment formula and optical indicator composition, the optical indicator composition comprising a fluorophore-based indicator with a diaminoethylbenzene nucleus containing a stabilizing agent, the optical indicator composition being soluble in the treatment formula, visible under ultraviolet light and not reactive with the treatment formula, the blend applied to the non-woven fabric in amounts which are effective to make the indicator visible under ultraviolet light and to allow the determination of the uniformity of the application of the blend and treatment formula to the non-woven fabric.

13. The non-woven fabric product according to claim 12, wherein the stabilizing agent is a diaminoethylbenzene-disulphonic acid or derivative thereof.

14. The non-woven fabric product according to claim 12, wherein the non-woven fabric product is selected from the group consisting of topsheet, backsheet, transfer layer, anti-leakage lateral cuff or barrier, fastening tape, or combination thereof.

* * * * *